July 30, 1935. A. FREY Plant Pat. 128
FREESIA (RED)
Filed April 18, 1934
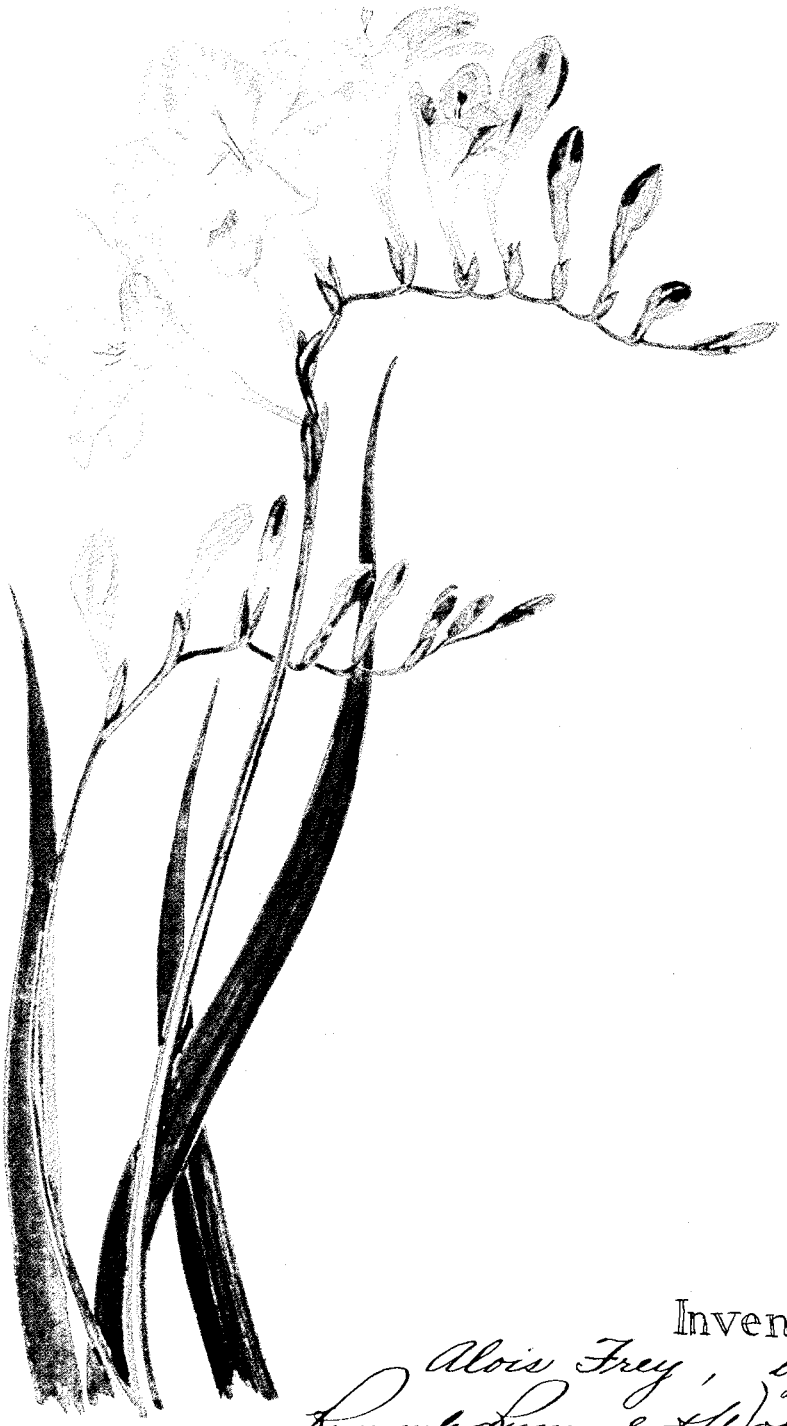
Inventor
Alois Frey, by
Kummler Kummler & Woodworth,
Attorneys Patented July 30, 1935

Plant Pat. 128

UNITED STATES PATENT OFFICE

128

FREESIA (RED)

Alois Frey, San Fernando, Calif.

Application April 18, 1934, Serial No. 721,148

1 Claim. (Cl. 47—60)

This invention relates to improvements in colored or tinted freesias.

The main objects of my invention are to provide an improved freesia of a richly colored type having a profusion of large widely-opened blossoms of a pleasing Tyrian rose shade on long sturdy stems, a goodly number of which are open at one time; and to stabilize and develop other characteristics of the herein described plant for use as a florist stock article, and having especial regard to vigor, My new freesia is the result of numerous crosses of unnamed parentage, carefully selected and crossed with these objects in view.

The accompanying illustration shows (in the original drawing) the new freesia approximately full size and true in color.

A very desirable characteristic of this new variety of freesia is the firm substance of the petals. Although the blossoms open widely, they are not readily damaged in shipping or other handling, which makes it commercially desirable.

The following is a detailed description of this new variety of freesia:

On a single spike as many as eight to ten flowers are ordinarily to be found, although this number will vary. From four to five flowers are in full bloom at a time with one or more partly opened and showing color. The flowers are borne upright along a sturdy axis which is bent abruptly at right angles to the vertical main stem. The fully opened flowers measure approximately two inches across the top and two inches high from the axis, although some blooms may appear of slightly larger dimensions. The perianth is funnel-shaped and tapers gracefully.

Many of the flowers have as many as eight lobes or segments which are broad, rounded and overlapping, very firm in substance, and which turn back at right angles to the funnel-shaped tube or perianth, thereby showing to advantage the harmonious blending of colors. In the upper portion of the petals, both inside and outside, the color tone according to Ridgeway's Color Standard is "Tyrian rose", shading down the petal to "Tyrian pink", (Ridgeway Plate XII), these colors being shot with delicate streaks of "cadmium yellow" (Ridgeway Plate III) in varying degrees, becoming solid yellow down into the perianth.

The coloring of the outside of the perianth is a soft blending of the two Tyrian shades, becoming yellow midway, and finally showing at the lowest part as "apple green" (Ridgeway Plate III) with tiny streaks of red.

The first color that shows in the buds is dahlia purple (Ridgeway Plate XII), later turning to "pansy purple" (Ridgeway Plate XII).

That part of the stem which supports the flowers is "cedar green" (Ridgeway Plate VI), while the vertical or supporting stem is "parrot green" (Ridgeway Plate VI).

This variety of freesia is very fragrant, having a penetrating yet pleasing exotic odor.

This plant is a vigorous grower and under average conditions will grow thirty inches high, or more, with usually three or four laterals. The mature leaves are approximately sixteen inches long, three-eighths inches wide at their widest points and rich green in color.

The main stem, or peduncle, which supports the flow group is ordinarily from seven and three-quarters inches long from the uppermost lateral to the first flower and approximately twelve inches long to the end of the stem.

The main characteristics which in combination quickly distinguish my new variety from all other known varieties of freesias are:

(1) Relatively large size of plants and flowers;

(2) The large number of flowers produced on a spike with four or more open at the same time;

(3) The distinctive Tyrian shades and streaked coloring of the flowers;

(4) Very widely opened flowers showing a broad expanse of color;

(5) Very firm texture of the petals, thus enabling the flowers to withstand handling and shipping unusually well;

(6) Long strong stems, and long lateral spikes;

(7) The delicacy of its perfume;

(8) Vigorous growing and blooming qualities.

I claim:

The variety of freesia as herein shown and described, characterized particularly by a predominating Tyrian red and yellow coloring, and the large size and number of blossoms on long spikes, flat opening firm flower segments and vigorous growth.

ALOIS FREY.